United States Patent [19]
Leight et al.

[11] Patent Number: 5,996,123
[45] Date of Patent: Dec. 7, 1999

[54] EARMUFF FOR NOISE BLOCKING

[75] Inventors: Howard S. Leight, Malibu; Edwin Woo, Chula Vista, both of Calif.

[73] Assignee: Bacon USA Safety, Inc., San Deigo, Calif.

[21] Appl. No.: 09/174,301

[22] Filed: Oct. 16, 1998

[51] Int. Cl.[6] .................................................. A61F 11/14
[52] U.S. Cl. .............................. 2/209; 181/129; 128/867
[58] Field of Search ....................... 2/209, 423; 181/129; 128/864, 867, 866; 381/187, 183

[56] References Cited

U.S. PATENT DOCUMENTS

| | | | |
|---|---|---|---|
| 4,774,938 | 10/1988 | Leight | 128/864 |
| 4,852,683 | 8/1989 | Killion | 181/130 |
| 4,856,118 | 8/1989 | Sapiejewski | 2/209 |
| 4,905,322 | 3/1990 | Aileo et al. | 2/209 |
| 5,020,163 | 6/1991 | Aileo et al. | 2/209 |

*Primary Examiner*—Michael A. Neas
*Attorney, Agent, or Firm*—Leon D. Rosen

[57] ABSTRACT

A noise blocking earmuff is described, which has a better noise blocking ability and which is more comfortable than prior earmuffs. The earmuff includes a cup-shaped shell (20), a cushion (22) that surrounds the open inner end of the shell and which presses against the head of the wearer, and an inside sound-absorber (26) lying in the shell. The cushion is formed of slow recovery material which has a rebound of no more than about 10 percent, to more comfortably and completely conform the cushion to the area of the wearer's head that the cushion presses against. The inside sound absorber includes a layer (50) of resilient felted foam for blocking higher frequency sounds, and a layer (52) of unfelted foam for blocking lower frequency sounds, to obtain a better overall noise blocking capability.

6 Claims, 3 Drawing Sheets

EARMUFF FOR NOISE BLOCKING

BACKGROUND OF THE INVENTION

Noise blocking earmuffs include a pair of earmuffs that are pressed against opposite sides of the wearer's head by a band. Each earmuff includes a cup-shaped shell with an open inner end, and with a largely ring-shaped cushion that receives the middle and upper portions of the outer ear of the person. A sound absorber lies in the shell. Both the cushion and sound absorber are generally formed of ordinary resilient foam. Two factors that are of great importance are the comfort of the person wearing the earmuffs, and the noise blocking ability of the earmuff. The noise blocking ability is generally rated with an NRR number given by an independent testing laboratory, with a higher NRR number (Noise Reduction Ratio, measured by a standard procedure of American National Standard 53.19-1974) representing better noise blocking ability. The highest NRR number for earmuffs that applicant knows of is 30. An earmuff with an even higher NRR rating number, which was also very comfortable for the wearer, would be of value.

SUMMARY OF THE INVENTION

In accordance with one embodiment of the invention, an earmuff is provided which is comfortable and especially effective in blocking noise. The earmuff includes a cup-shaped shell with an open inner end that supports a cushion for pressing against the head of the wearer, and with a sound absorber lying within the cup. Applicant constructs the cushion primarily of a resilient foam slow recovery material, which is a material having a recovery of no more than about 10 percent. Applicant prefers to use a moderate slow recovery material that has a recovery of between about 5 percent and 10 percent. The sound absorber within the cup is preferably formed by a plate or layer of felted foam and another layer of unfelted foam. The felted foam is effective in blocking sound of higher frequencies such as above about 1,000 Hz, while the unfelted foam is especially useful in blocking lower frequencies such as below 1,000 Hz. The combination of the two results in good noise blocking capability for all frequencies of interest.

The novel features of the invention are set forth with particularity in the appended claims. The invention will be best understood from the following description when read in conjunction with the accompanying drawings.

DESCRIPTION OF THE PREFERRED EMBODIMENTS

Figure 1:
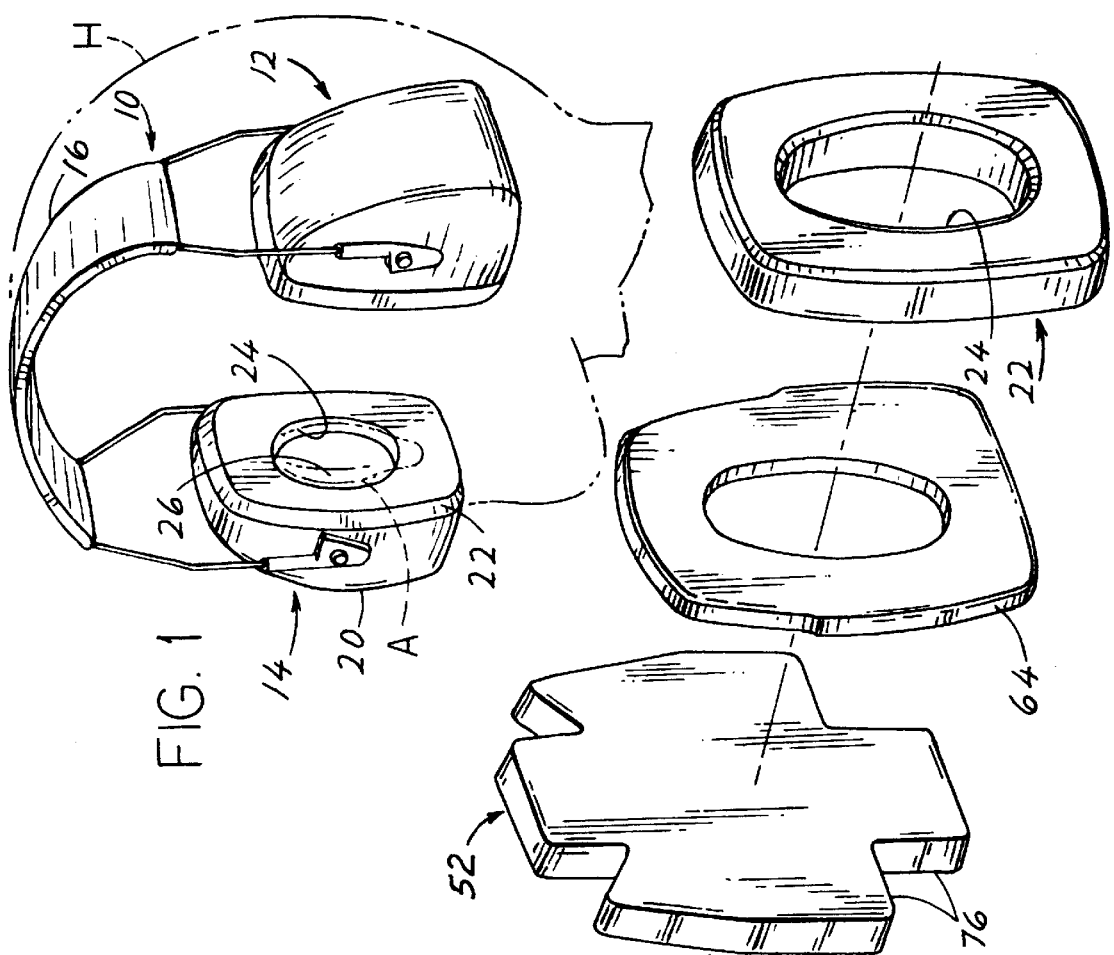
FIG. 1 is an isometric view showing an earmuff assembly of the present invention worn by a person.
Figure 4:
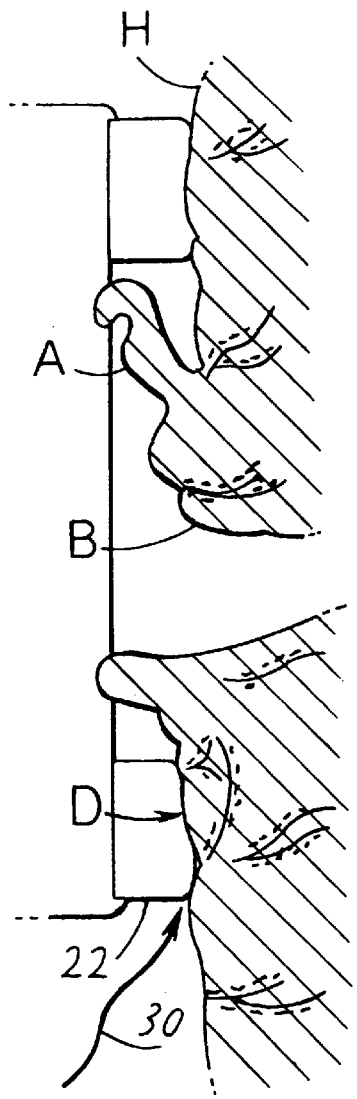
FIG. 4 is a section view of the cushion of the earmuff of FIG. 3, shown pressing against the wearer's head.
Figure 3:
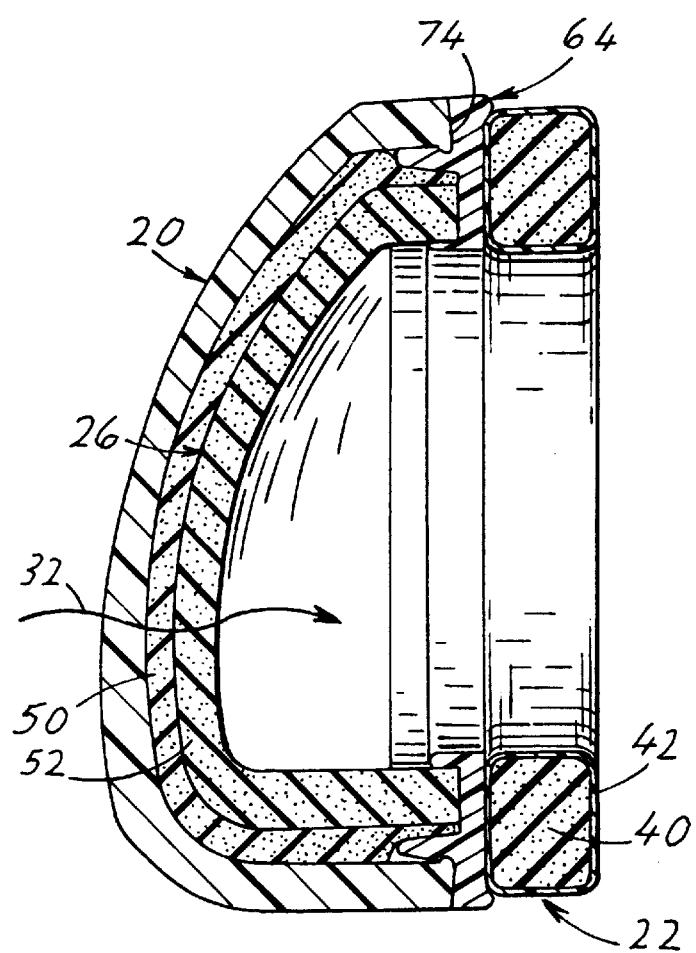
FIG. 3 is a sectional side view of the earmuff in FIG. 2, shown fully assembled.

FIG. 1 illustrates an earmuff assembly 10 which is designed to fit over the head H of a person, the assembly including a pair of earmuffs 12, 14 and a band 16 that connects them and presses them against opposite sides of the head of the person. Each earmuff includes a cup-shaped shell 20 and a cushion 22 at the open inner end of the shell. The middle and upper portions of the outer ear A of the person are received within an opening 24 of the cushion. A sound absorber 26 lies deep within the cup. As shown in FIGS. 3 and 4, the cushion 22 prevents sound waves at 30 from reaching the ear canal B of the person by the sound passing between the cushion 22 and the outer ear A (that part outside the ear canal and exposed to the environment) of the person. The cushion also blocks sound that would pass directly through the cushion to the ear canal. The sound absorber 26 prevents sound from passing along paths 32 through the shell 20 to the ear canal B.

Both the cushion 22 and the sound absorber 26 are formed of resilient polyurethane foam, as they have been previously. However, applicant selects particular foams or foam combinations, that result in greater comfort and better noise blocking.

The cushion 22 includes a core loop 40 of resilient foam and a soft rubber-like covering 42 that resists penetration by water, sweat, etc., and that provides a smooth and attractive finish. One type of resilient foam, referred to as "slow recovery foam" has the property that when compressed and with the compression force then rapidly released, the foam does not immediately return to its original shape. Such slow recovery materials have been used for earplugs that are rolled in the fingers to a small diameter for easy insertion into the ear canal, and which expand after perhaps 10 seconds within the ear canal to then seal it. Such slow recovery foam for earplugs may be referred to as very slow recovery foam, because it takes a plurality of seconds after compression to ⅕th its previous thickness for return to ¾ its previous thickness. Such very slow recovery is achieved by mixing latex into the foamable material, with the latex causing opposite walls of foam cells to temporarily stick together when compressed. Another type of slow recovery foam can be referred to as a moderate slow recovery foam, in that it returns from ⅕ to ¾ of its thickness in less than 2 seconds. Such moderate recovery foam generally does not include latex to slow the recovery. Such moderate recovery foam has been used to provide a mattress for invalid persons, in that it increases the comfort and reduces bedsores for such persons. One type of test is a drop test, where a ball is dropped onto a plate of foam. When such a ball is dropped on ordinary resilient foam, there is about a 40 to 50 percent recovery of the ball (it bounces up to a height that is about 40 to 50 percent of the height from which the ball was dropped). The rebound for a very slow recovery material, is typically about 2 to 3 percent. The rebound for moderate slow recovery material is about 5 to 10 percent (between 4 percent and 12 percent).

Applicant prefers to form the core loop 40 of the cushion 22, of a moderate slow recovery foam. When the cushion presses against the person's head, irregularities in the person's head, especially at the area D near the earlobe, result in concentrated forces and consequent discomfort to the person. Slow recovery material, and especially moderate slow recovery material, has a property that pressing forces are more evenly distributed. This results in more uniform distribution of forces and, as occurs when invalid persons lie on a mattress of the material, results in greater comfort for the person. Applicant believes that this better distribution of the pressing forces with which the earmuff is pressed against the head, also results in better sound sealing, in that the forces at non-projecting locations on the head is increased, just as it is decreased for projecting portions of the head.

The moderate slow recovery foam enables a person to seat the earmuffs against his/her head (including against the earlobe) and wait only about a second to judge the level of comfort (and possibly also sound blocking effectiveness). If not comfortable, the earmuffs can be moved a few times until comfort is sensed. If very slow recovery foam were used then it would take many seconds before comfort (and noise blocking) could be judged in each position, and many people will not wait that long.

Applicant constructs the sound absorber 26 of two layers 50, 52 of different types of resilient foam (which are preferably not of slow recovery material). One layer 50 is formed of felted resilient foam, while the other layer 52 is formed of unfelted resilient foam. It is noted that plates of foam are commonly formed by pouring the foamable ingredients onto a flat surface and allowing it to foam and set. The cells, which are open (by the addition of surfactants) are vertically elongated. Such foam can be felted by compressing it under heat as by compressing a polyurethane foam at 2,000 psi and a temperature of 350–400° F. The resulting felted foam has a density that is commonly two to three times that of the original foam, and measurements on it show that it has different sound-blocking characteristics.

Figure 5:
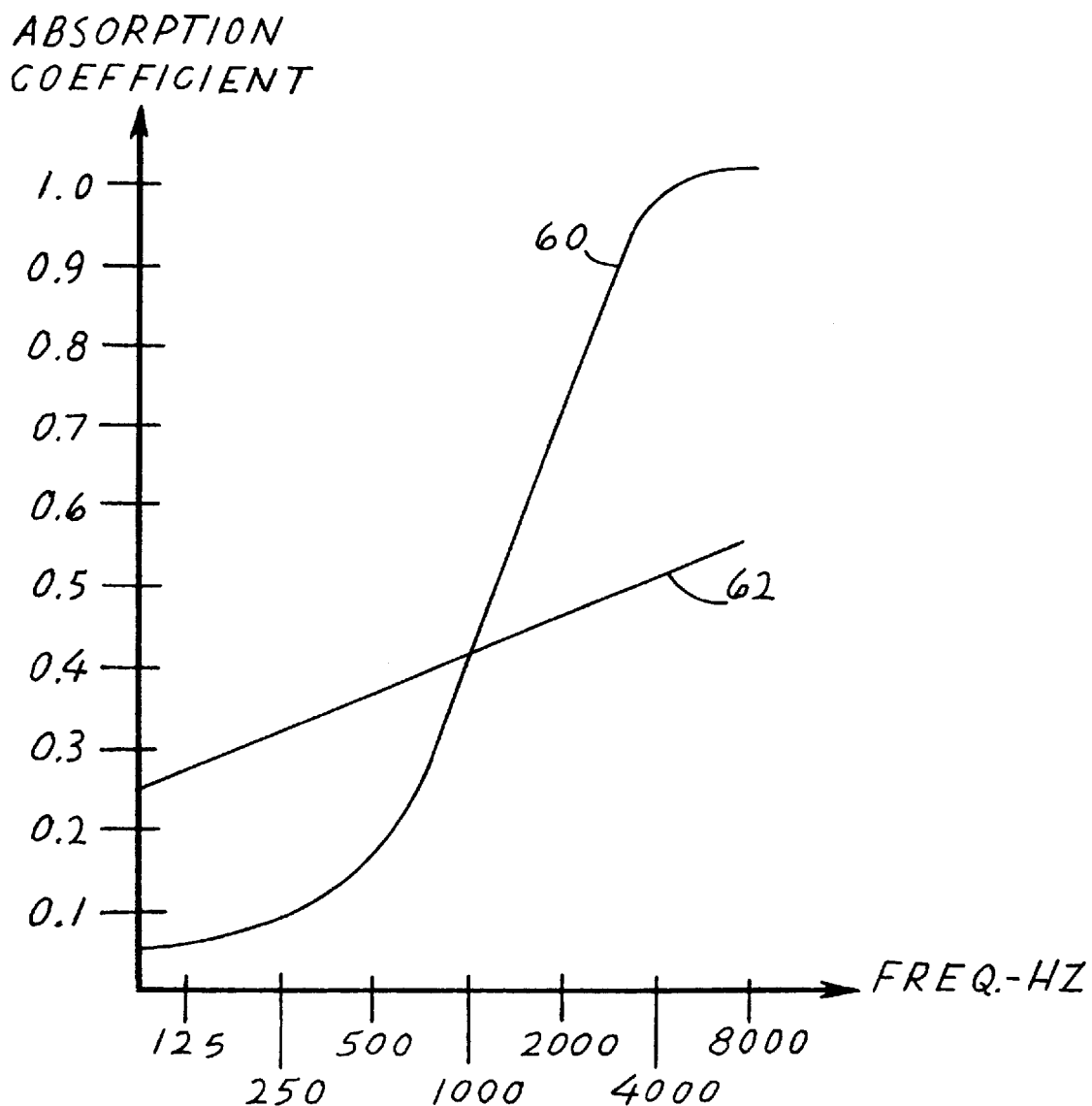
FIG. 5 is a graph with graph lines showing variation in absorption coefficient with frequency for two different types of resilient foam materials.

FIG. 5 shows the approximate sound-blocking characteristics of two types of foam. Graph line 60 represents the characteristics of a quarter-inch thick plate of polyurethane felted foam which has a density of 1.6 pounds per square foot. It can be seen that the absorption coefficient, which represents the amount of sound that is blocked, is low at low frequencies and increases rapidly between about 500 Hz and about 3,000 Hz, to a high level. Graph line 62 represents the sound-blocking characteristics of an ordinary (unfelted) resilient polyurethane foam, which has sound-blocking characteristics that change only slowly with frequency. Below about 1,000 Hz, the unfelted foam has a higher sound blocking coefficient than does the felted foam.

Applicant uses both a layer of felted foam and a layer of unfelted foam to obtain good noise-blocking characteristics throughout the frequency range which is most likely to cause damage to the ears, which is from about 125 Hz to about 8,000 Hz. As shown in FIG. 5, below about 1,000 Hz, the noise-blocking characteristics are only slightly above those of the unfelted foam at 62, while above 1,000 Hz the noise-blocking characteristics are those of the felted foam, at 60.

Although thicker foam is desireable, only about ¾ inch thick foam can fit into the shell 20 and still leave clearance to avoid pressing against the top of the outer ear of a person whose ears project slightly more than normal. As shown in FIG. 3, the felted foam layer 50 has a thickness of ¼ inch, while the unfelted foam 52 has a thickness of about ½ inch. Both layers are slightly compressed within the shell 26 to hold them in place. The felted foam thickness is preferably less than three-quarters of the unfelted foam thickness. The relatively small thicknesses leave room in the cup to receive the upper portion of the outer ear.

Figure 2:
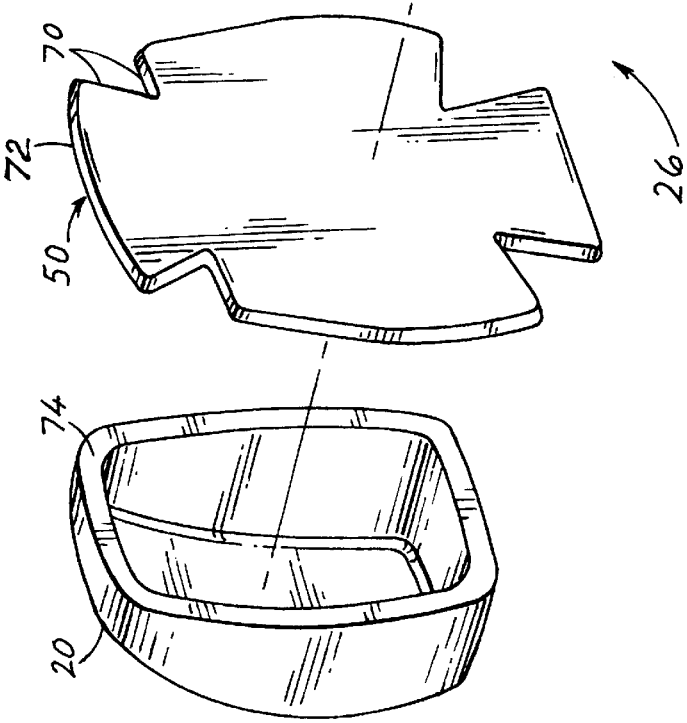
FIG. 2 is an exploded isometric view of one of the earmuffs of the assembly of FIG. 1.

FIG. 2 shows the actual shapes of the shell 20, the plate or layer 50 of felted foam, the plate or layer of unfelted foam 52, a retention flange 64, and the cushion 22. The felted layer 50 and unfelted layer 52 are both pushed into place in the shell. Adjacent surface 70 of the wings 72 press together while the tips of the wings press against the flange 64. Similarly, surfaces 74 of the unfelted foam press together and the tips of the wings 76 press against the flange 64. The retention flange 64 is snapped into place against the inner face 74 of the shell. Finally, the cushion 22 is held by adhesive to the outer face of the retention flange 64.

Tests on an earmuff of the construction described and illustrated, show that it had an NRR rating of 31.6, which is significantly better than the best rating of 30 known to applicant for an earmuff. Applicant found that this highest rating was achievable with a force of the earmuff against the wearer's head, of 11 newtons. The best previous earmuff that applicant knows of achieved an NRR rating of 30 when pressed with a force of 12 newtons against the head of a person. Of course, a lower force increases comfort.

Thus, the invention provides an earmuff which has better sound-blocking ability than previous earmuffs, and which wearers have reported to be more comfortable than the best previous earmuffs. The cushion for the earmuff is formed of a slow recovery material, and preferably a moderate slow recovery material, which is a material having a recovery of about 5% to 10% in a drop test. The sound absorbing material in the shell of the earmuff includes two layers of different materials, one layer being of resilient felted foam material, which has very good noise blocking capacity at higher frequencies but not at lower frequencies, and the other layer being of unfelted resilient foam material which has moderately good noise blocking ability at all frequencies including lower frequencies.

Although particular embodiments of the invention have been described and illustrated herein, it is recognized that modifications and variations may readily occur to those skilled in the art, and consequently, it is intended that the claims be interpreted to cover such modifications and equivalents.

What is claimed is:

1. A noise blocking earmuff comprising:

an earmuff shell having an open inner end and a closed outer end;

a cushion mounted on said inner end of said shell, said cushion having a central opening for receiving most of the outer ear of a person and said cushion extending completely around the central opening;

an inside sound-absorber lying in said shell outward of said cushion;

said cushion being formed of slow recovery material which has a rebound of no more than about 10%, whereby to more comfortably and more completely conform the cushion to the area of wearer's head that the cushion presses against.

2. The earmuff described in claim 1 wherein:

said slow recovery foam of said cushion is a moderately slow recovery foam which has a rebound of about 5 to 10%, whereby to provide an immediate indication of whether the cushion is well seated on the wearer's head.

3. The earmuff described in claim 1 wherein:

said inside sound absorber includes a layer of resilient felted foam and a layer of resilient unfelted foam which each blocks substantially the entire cup, whereby to block both high and low frequencies of sound.

4. A noise blocking earmuff comprising:

an earmuff shell having an open inner end and a closed outer end;

a cushion mounted on said inner end of said shell, said cushion having a central opening for receiving most of the outer ear of a person and said cushion extending completely around the central opening;

an inside sound-absorber lying in said shell outward of said cushion;

said inside sound absorber including a layer of resilient felted foam to thereby block higher frequency sound, and a layer of resilient unfelted foam to thereby also block lower frequency sound, with said layers each blocking substantially the entire cup area through which sound could pass through the central opening of said cushion.

5. The noise blocking earmuff described in claim 4 wherein:

said layer of resilient felted foam is no more than ¾ the thickness of said unfelted foam.

6. The noise blocking earmuff described in claim 4 wherein:

said cushion is formed of slow recovery material which has a rebound of between about 5% and 10%.

\* \* \* \* \*